United States Patent
Oren et al.

(10) Patent No.: US 8,328,843 B2
(45) Date of Patent: Dec. 11, 2012

(54) FINGER MOUNTING FOR SURGICAL INSTRUMENTS PARTICULARLY USEFUL IN OPEN AND ENDOSCOPIC SURGERY

(75) Inventors: Ran Oren, Kibbutz Gaaton-Doar-Na Oshrat (IL); Eran Zakai, Moshav Yodfat-Doar-Na Misgav (IL); Dan Moor, Kibbutz Gaaton-Doar-Na Oshrat (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 186 days.

(21) Appl. No.: 12/815,442

(22) Filed: Jun. 15, 2010

(65) Prior Publication Data
US 2010/0249826 A1      Sep. 30, 2010

Related U.S. Application Data

(62) Division of application No. 11/729,939, filed on Mar. 30, 2007, now abandoned.

(51) Int. Cl.
*A61B 17/00* (2006.01)
*A61B 17/50* (2006.01)

(52) U.S. Cl. ........................................ 606/205; 606/210

(58) Field of Classification Search .................. 606/190, 606/198, 205, 206, 207, 208, 209, 210, 211, 606/51–52, 131–132; 7/121; 223/101; 443/162; 81/177.344, 119, 176.3, 177.3, 349, 383.5, 81/418, 453; 294/99.1, 99.2, 94–96; 30/232, 30/291, 298
See application file for complete search history.

(56) References Cited

U.S. PATENT DOCUMENTS

| 216,918 | A | * | 6/1879 | Wales ........................... 294/99.2 |
| 1,058,234 | A | * | 4/1913 | Hamilton ....................... 132/321 |
| 2,685,880 | A | * | 8/1954 | Curutchet ..................... 606/205 |
| 2,781,760 | A | | 2/1957 | Baer |
| 3,293,958 | A | | 12/1966 | Smith |
| 3,392,727 | A | | 7/1968 | Hanlon |
| 3,981,308 | A | | 9/1976 | Schlein |

(Continued)

FOREIGN PATENT DOCUMENTS
WO      WO 2008/120190      10/2008
(Continued)

OTHER PUBLICATIONS

International Preliminary Report on Patentability Dated Dec. 10, 2009 From the International Bureau of WIPO Re.: Application No. PCT/IL2008/000417.

(Continued)

*Primary Examiner* — Gary Jackson
*Assistant Examiner* — Jonathan Hollm

(57) ABSTRACT

A surgical instrument assembly particularly useful in endoscopic surgery includes a sleeve to be received on a user's finger and integrally formed at one side with a socket; and an elastic member formed at a mid-portion thereof with a pair of arms elastically-urged to a closed position to serve as a pair of forceps for grasping objects. The elastic member is further integrally formed at one end with a mounting strip folded to overlie said pair of arms for mounting the elastic member within said socket, and at the opposite with a finger-engageable strip folded to underlie said pair of arms. The finger-engageable strip terminates in a cam element movable by the elasticity of the elastic member between said pair of arms to cam them apart to an open position to release a grasped object.

4 Claims, 6 Drawing Sheets

U.S. PATENT DOCUMENTS

| | | | |
|---|---|---|---|
| 4,177,698 A | | 12/1979 | Greneker |
| D255,715 S | | 7/1980 | Markham |
| 4,318,313 A | | 3/1982 | Tartaglia |
| 4,644,651 A | | 2/1987 | Jacobsen |
| 4,726,371 A | * | 2/1988 | Gibbens ........................ 606/174 |
| D299,168 S | | 12/1988 | Bergström et al. |
| 4,955,515 A | | 9/1990 | Brull |
| 5,125,923 A | | 6/1992 | Tanner et al. |
| 5,329,832 A | | 7/1994 | Tegethoff |
| 5,405,353 A | | 4/1995 | Randall |
| 5,441,494 A | | 8/1995 | Ortiz |
| 5,498,256 A | | 3/1996 | Furnish |
| 5,511,546 A | | 4/1996 | Hon |
| 5,514,153 A | | 5/1996 | Bonutti |
| 5,640,977 A | | 6/1997 | Leahy et al. |
| 5,693,041 A | | 12/1997 | Murphy-Chutorian |
| 5,697,889 A | | 12/1997 | Slotman et al. |
| 5,803,322 A | | 9/1998 | Boone et al. |
| 5,876,420 A | | 3/1999 | Noll et al. |
| 5,925,064 A | | 7/1999 | Meyers et al. |
| 5,925,065 A | | 7/1999 | Totakura et al. |
| 6,165,184 A | | 12/2000 | Verdura et al. |
| 6,213,952 B1 | | 4/2001 | Finarov et al. |
| 6,419,926 B2 | | 7/2002 | Kodama et al. |
| 6,944,914 B2 | | 9/2005 | Tillim |
| 7,211,091 B2 | | 5/2007 | Fowler et al. |
| 2003/0220542 A1 | | 11/2003 | Belson et al. |
| 2004/0153020 A1 | | 8/2004 | Bartel et al. |
| 2004/0193211 A1 | | 9/2004 | Voegele et al. |
| 2004/0199204 A1 | | 10/2004 | Voegele et al. |
| 2004/0231167 A1 | | 11/2004 | Miklos |
| 2005/0240219 A1 | | 10/2005 | Kahle et al. |
| 2005/0267519 A1 | | 12/2005 | Tillim |
| 2007/0013681 A1 | | 1/2007 | Chou |
| 2007/0239202 A1 | | 10/2007 | Rodriguez |
| 2007/0250111 A1 | | 10/2007 | Lu et al. |
| 2008/0243174 A1 | | 10/2008 | Oren et al. |
| 2008/0243177 A1 | | 10/2008 | Oren et al. |
| 2008/0243178 A1 | | 10/2008 | Oren et al. |

FOREIGN PATENT DOCUMENTS

| | | |
|---|---|---|
| WO | WO 2008/120191 | 10/2008 |
| WO | WO 2008/120192 | 10/2008 |

OTHER PUBLICATIONS

International Preliminary Report on Patentability Dated Jan. 28, 2010 From the International Bureau of WIPO Re.: Application No. PCT/IL2008/000415.

International Preliminary Report on Patentability Dated Jan. 28, 2010 From the International Bureau of WIPO Re.: Application No. PCT/IL2008/000416.

International Search Report Dated Oct. 1, 2008 From the International Searching Authority Re.: Application No. PCT/IL08/00416.

International Search Report Dated Sep. 22, 2008 From the International Searching Authority Re.: Application No. PCT/IL08/00417.

Notice of Alllowance Dated Apr. 21, 2008 From the United States Patent and Trademark Office Re:. U.S. Appl. No. 29/285,475.

Notice of Allowance Dated Jan. 14, 2008 From the United States Patent and Trademark Office Re.: U.S. Appl. No. 29/278,450.

Notice of Allowance Dated Jan. 14, 2008 From United States Patent and Trademark Office Re.: U.S. Appl. No. 29/278,447.

Notice of Allowance Dated Apr. 21, 2008 From United States Patent and Trademark Office Re.: U.S. Appl. No. 29/285,475.

Notice of Allowance Dated Jan. 25, 2008 From United States Patent and Trademark Office Re.: U.S. Appl. No. 29/285,474.

Official Action Dated Sep. 4, 2009 From the US Patent and Trademark Office Re.: U.S. Appl. No. 11/729,939.

Official Action Dated Aug. 7, 2009 From the US Patent and Trademark Office Re.: U.S. Appl. No. 11/729,942.

Official Action Dated May 13, 2009 From the US Patent and Trademark Office Re.: U.S. Appl. No. 11/729,939.

Official Action Dated Mar. 15, 2010 From the US Patent and Trademark Office Re.: U.S. Appl. No. 11/729,939.

Official Action Dated Oct. 28, 2009 From the US Patent and Trademark Office Re.: U.S. Appl. No. 11/729,919.

Response Dated Dec. 3, 2009 to Official Action of Sep. 4, 2009 From the US Patent and Trademark Office Re.: U.S. Appl. No. 11/729,939.

Written Opinion Dated Oct. 1, 2008 From the International Searching Authority Re.: Application No. PCT/IL08/00416.

Written Opinion Dated Sep. 22, 2008 From the International Searching Authority Re.: Application No. PCT/IL08/00417.

* cited by examiner

FINGER MOUNTING FOR SURGICAL INSTRUMENTS PARTICULARLY USEFUL IN OPEN AND ENDOSCOPIC SURGERY

RELATED APPLICATIONS

This application is a divisional of U.S. patent application Ser. No. 11/729,939 filed Mar. 30, 2007, the contents of which are incorporated herein by reference in their entirety.

FIELD AND BACKGROUND OF THE INVENTION

The present invention relates to finger-mountings for surgical instruments for use in both open and endoscopic surgery. The invention also relates to such finger-mountable surgical instruments.

In an open surgery procedure, an incision is made through the skin, and the tissues overlying the surgical site are retracted in order to expose an area large enough to allow for access and orientation by direct vision. The surgeon may use a wide range of instruments to perform the specific procedure, and may also use the surgeon's fingers to touch organs and receive tactile feedback. However, fingers lack the delicacy to pick up fine tissue; they require making larger divisions when dissecting tissues; and they are subject to injury when holding tissue if sharp instruments or energy modalities, such as ultrasound or RF, are used in the treatment at the surgical site.

In recent years, more and more procedures are being performed endoscopically. Endoscopy is a minimal invasive surgical procedure in which illumination, cameras and surgical tools are inserted into the patient's body via small incisions through the skin, and are manipulated externally, guided by the image displayed on a TV monitor. For the patient, trauma is minimized, and healing time and length of stay in hospital are shortened. Particularly, laparoscopy—endoscopy in the abdominal cavity—is being widely used both for diagnosis and for performing full surgical procedures.

However, several difficulties are inherent in this technique. Thus, considerable skill and experience are required to position the instruments spatially relative to internal organs while viewed in a two-dimensional monitor. Also, the field of vision displayable on the monitor is narrow making orientation even more difficult. In addition, it is hard to control the instruments because of their length, which is typically about 350 mm from the handles outside the body to the tip that actually performs the operations within the body cavity; this length is needed to reach the organs within the abdomen when the cavity is insufflated as required by the technique. Moreover, direct contact between the organs and the surgeon's hand is not possible, so that tactile feedback is lost.

Recently, a modified laparoscopic technique has evolved which is referred to as Hand-Assisted Laparoscopic Surgery (HALS), in which one hand of the surgeon has access to the body cavity while maintaining insufflation. This technique, as described for example in U.S. Pat. No. 5,640,977 to Patrick Leahy et al, is now an alternative procedure of choice. As only a relatively small additional incision is required, just sufficient for admitting the surgeon's hand, the advantages of minimal invasiveness are preserved. For the surgeon, less training is required because the presence of his/her hand in the body cavity allows palpation of internal organs, biophysical feedback, and easier manipulation of various instruments within the body cavity while viewing the TV monitor.

With the advancement of the HALS technique, a need arose for instruments which could be mounted directly onto the fingers of the hand within the body cavity, i.e., the "ported" hand. Miniature forceps, graspers, scissors, dissectors, probes, retractors, etc., modeled on existing instruments used in open surgery and mounted on the surgeon's finger, could perform delicate surgical tasks and aid the laparoscopic instruments introduced through the "keyhole" incisions. Obviously it would be advantageous to provide such instruments for use in open procedures as well as in "keyhole" procedures.

Several such instruments were suggested in U.S. Pat. No. 5,925,064 to Meyers et al, and US Application 20040193211 to Voegele et al. However, all the instruments described therein must be fixed to the finger outside of the body. Therefore, in HALS procedures the hand must be withdrawn through the port for changing instruments, which limits the advantages possible by this procedure.

OBJECT AND BRIEF SUMMARY OF THE PRESENT INVENTION

An object of the present invention is to provide a finger mounting for a surgical instrument which enables the surgical instrument to be mounted on the surgeon's finger by other fingers in the same hand to carry the surgical instrument, thereby eliminating the need for withdrawing the hand from the body cavity for purposes of mounting or changing surgical instruments. Another object of the invention is to provide such finger-mountable surgical instruments.

According to a broad aspect of the present invention, there is provided a surgical instrument assembly, comprising: a sleeve dimensioned to be received on the outer end of a finger of a user and having an open proximal end for application to the outer end of the user's finger, an open distal end for exposing the outer tip of the user's finger when mounted thereon, and an inner diameter which decreases from said proximal end to said distal end for facilitating the application of the sleeve to the user's finger;

said sleeve being of an elastic material, having a longitudinal split along its length to permit its diameter to be increased in order to accommodate fingers of different thicknesses, and integrally formed at one side with a socket for receiving a surgical instrument;

and an elastic member integrally formed as a mid-portion thereof with a pair of arms elastically-urged to a closed position to serve as a pair of forceps for grasping objects; said elastic member being further integrally formed at one end with a mounting strip folded to overlie said pair of arms for mounting the elastic member within said socket, and at the opposite with a finger-engageable strip folded to underlie said pair of arms; said finger-engageable strip terminating in a cam element movable by the elasticity of the elastic member between said pair of arms to cam them apart to an open position to release a grasped object.

According to further features in the described preferred embodiments, the longitudinal split is defined by two opposed edges having interengaging ribs and recesses of a length in the circumferential direction to accommodate a wide range of finger thicknesses without pinching. Such inter-engaging ribs and recesses not only assure firm gripping of the (gloved) fingers around the complete circumference of the sleeve, but also facilitate the manipulation of the instrument onto the user's finger without pinching the user's finger. In addition, the inner surface of the sleeve is formed with circumferentially-extending ribs to firmly grip the user's finger when the sleeve is applied thereto. In the described embodiments, the sleeve is made of an elastic plastic material.

According to further features in the described preferred embodiments, the sleeve is integrally formed at one side with a socket for receiving a surgical instrument. Various types of surgical instrument are described for purposes of example, including retractors, probes, and forceps.

According to another aspect of the present invention, there is provided a finger-mountable surgical instrument, comprising: a sleeve dimensioned to be received on the outer end of a finger of a user; and a pair of arms integrally formed at one side of the sleeve which arms are displaceable towards and away from each other to closed and open positions, respectively, for grasping and releasing objects.

According to yet another aspect of the present invention, there is provided a finger-mountable surgical instrument comprising: a sleeve dimensioned to be received in the outer end of a finger of a user, the sleeve being formed at one side with a socket; and a surgical instrument received in the socket.

As will be described more particularly below, the invention enables one or more finger-mountable surgical instruments to be enclosed within the surgeon's fist and introduced with the surgeon's fist through the port into the body cavity in the above-described HALS procedures. The instruments, when so introduced into the patient's body, can be easily applied to and removed from the finger of the ported hand of the surgeon by merely manipulating the fingers of the ported hand, as will be described below.

An additional advantage of the described preferred embodiments is that the finger-mountable sleeves, and also the instruments affixed thereto, can be produced in volume and at low cost, thereby permitting one-time use.

Further features and advantages of the invention will be apparent from the description below.

BRIEF DESCRIPTION OF THE DRAWINGS

The invention is herein described, by way of example only, with reference to the accompanying drawings, wherein.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Figure 1:
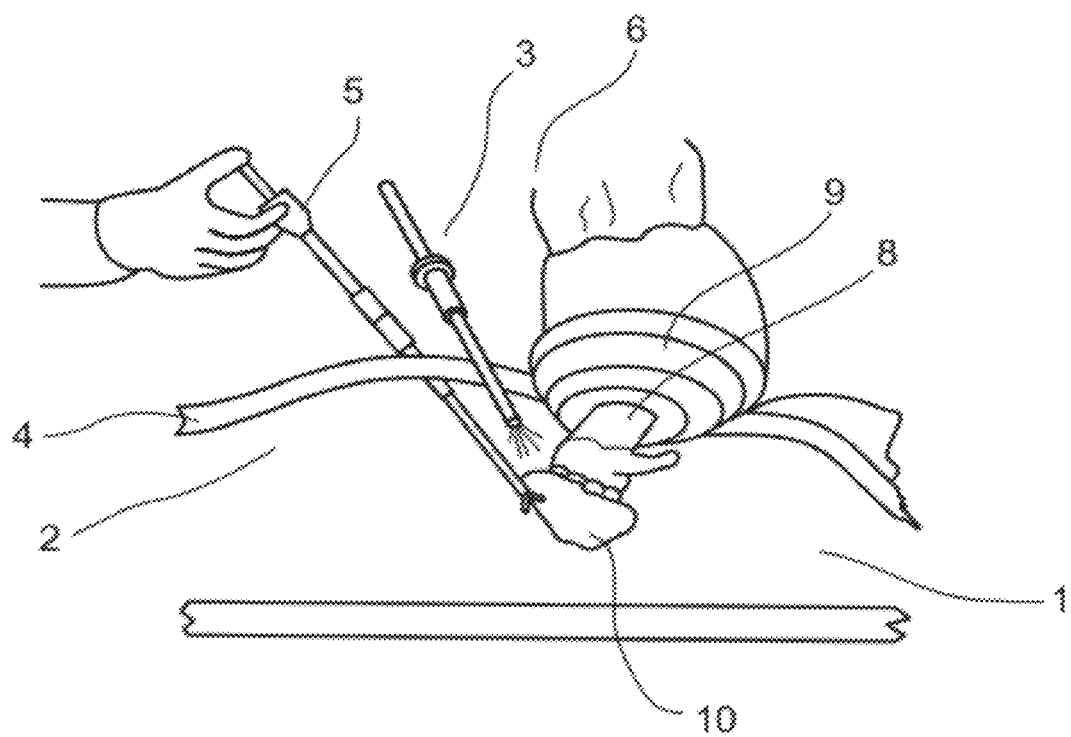
FIG. 1 schematically illustrates a hand-assisted laparoscopy procedure in which the invention is particularly useful.

FIG. 1 illustrates a patient 1 lying prone on an operating table, with the body (abdominal) cavity 2 insufflated to create free space for surgery. An endoscope 3 is inserted through the abdominal wall 4 to provide illumination and imaging. Through a second small incision, a grasping instrument 5 is introduced into the body cavity. The surgeon 6 manages the grasper with one gloved hand 7, while the other gloved hand 8, introduced through a hand port device 9, may be used for palpating an organ.

Figure 2:
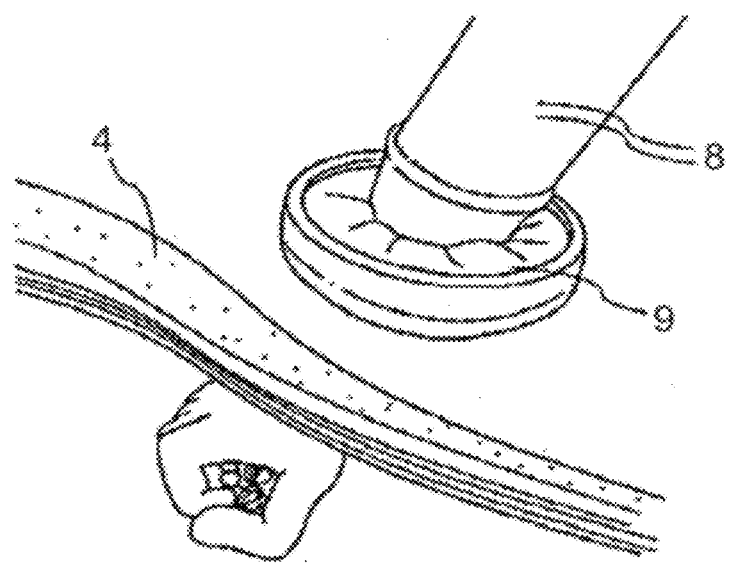
FIG. 2 illustrates the insertion of the surgeon's fist into the abdominal cavity holding a number of finger-mountable surgical instrument constructed in accordance with the present invention.

FIG. 2 illustrates the insertion of the gloved hand 8 through the hand port 9, which provides a seal around both the gloved hand and the abdominal wall 4. One or more finger-mounted surgical instruments are concealed in the closed fist, which protects them from causing damage when introduced through the port.

Figure 3:
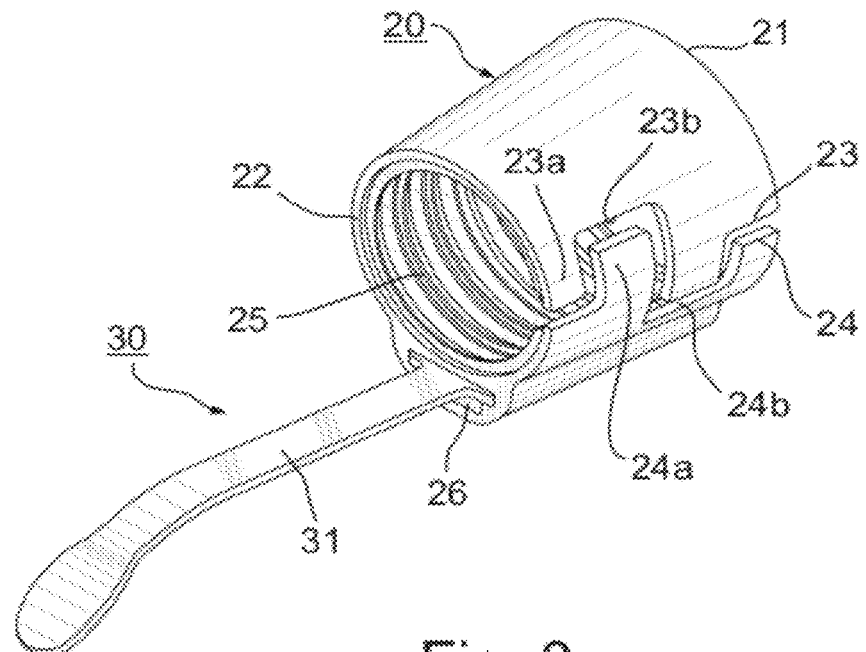
FIG. 3 illustrates a finger-mountable surgical retractor constructed in accordance with the present invention.

FIG. 3 illustrates a finger-mountable surgical instruments that may be included within the closed fist of the surgeon's hand shown in FIG. 2.

The finger-mountable surgical instrument illustrated in FIG. 3 includes a thimble or sleeve, generally designated 20, to be received on the outer end of a finger of the surgeon, and a surgical retractor, generally designated 30, fixed to the sleeve to project forwardly of the sleeve. Sleeve 20 has an open proximal end 21 (with respect to the surgeon) for application to the outer end of the surgeon's finger, and an open distal end 22 which exposes the outer tip of the surgeon's finger when mounted thereon. As seen in FIG. 3, sleeve 20 is of a tapered construction, having an inner diameter and an outer diameter decreasing from its proximal end 21 to its distal end 22, which facilitates the application of the sleeve to the surgeon's finger.

As further seen in FIG. 3, sleeve 20 is split along its longitudinal axis so as to define two opposed edges, 23, 24 confronting each other. Each of the two edges 23, 24 includes circumferentially-extending ribs (23a, 24a) and recesses (23b, 24b), interengaging each other. Sleeve 20 is made of an elastic, preferably plastic, material such that the longitudinal-split permits its diameter to be increased in order to accommodate fingers of different thicknesses. In addition the interengaging ribs and recesses not only better assure that the sleeve will firmly engage the entire outer surface of the surgeon's gloved finger when mounted thereon, but also facilitate the manipulation of the sleeve onto the user's finger without "pinching" the finger.

As further shown in FIG. 3, the inner surface of sleeve 20 is formed with circumferentially-extending ribs or rill-shaped undercuts, 25, which better assure firm gripping of the surgeon's gloved finger when the sleeve is mounted thereon.

Sleeve 20 illustrated in FIG. 3 is integrally formed at one side, namely the side adjacent the surface of the index finger 40 facing the user's thumb 41, with a socket 26 for receiving the surgical instrument 30 to project forwardly of the outer end of the user's index finger 40. In this case, socket 26 is in the form of a wide, rectangular passageway adapted to receive the flat shank 31 of surgical retractor 30. The flat shank 31 of surgical retractor 30 may be introduced into socket 26 via the distal end 22 of sleeve 20.

Figure 4:
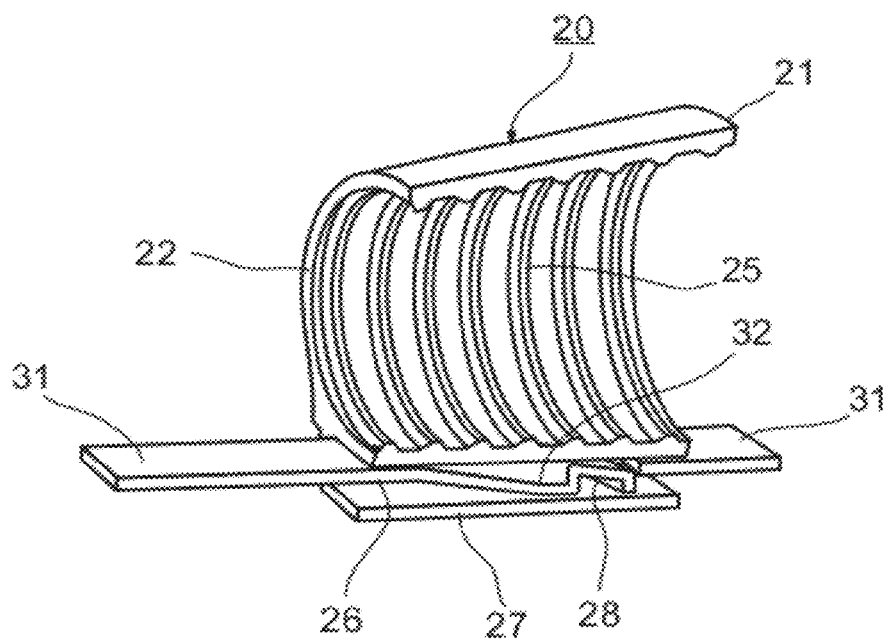
FIG. 4 is a fragmentary view of FIG. 3 illustrating the finger-mountable sleeve with the surgical retractor mounted and retained therein.

As shown in FIG. 4 socket 26 includes an outer wall 27 formed with a projection 28 which automatically seats within an elastic tongue 32 defining a detent in shank 31 of retractor 30 upon the insertion of the shank into the socket. The engagement of projection 28 with detent 32 may be a permanent snap-fit if the sleeve and retractor are intended for one-time use, or a releasable snap-fit if one (or both) of these elements is intended for multiple-use.

Figure 5:
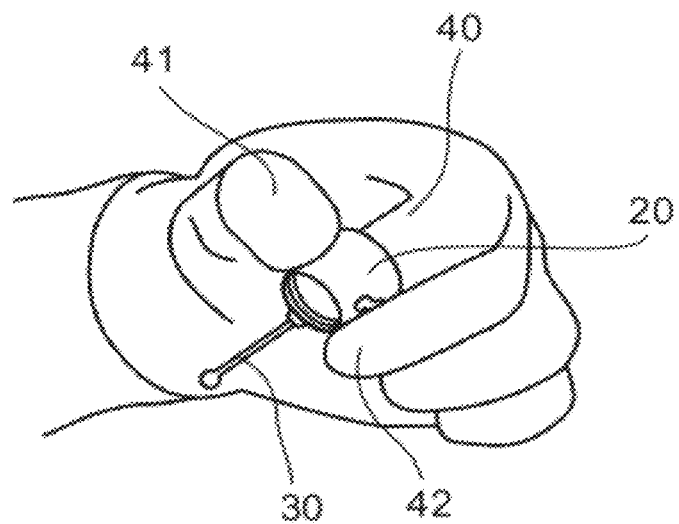
FIG. 5 illustrates the manner in which the illustrated finger-mountable retractor may be mounted on the surgeon's finger by merely manipulating other fingers of the surgeon's hand, thereby eliminating the need for withdrawing the surgeon's hand from the body cavity in a HALS procedure.

FIG. 5 illustrates how a finger-mountable instrument as illustrated in FIG. 3 may be gripped within the enclosed fist of a surgeon's gloved hand, when introduced through a hand port device 9 (FIG. 1), and conveniently applied to the index finger 40 of the surgeon's gloved hand by merely manipulating the sleeve using the thumb 41 and middle finger 42 of the surgeon's hand. Providing the socket 26 on the side of sleeve 20 adjacent the surface of the user's index finger 40 facing the user's thumb 41, also better enables the instrument received in the socket to be more conveniently manipulated by pressing the user's thumb against the socket or the instrument therein.

Figure 6:
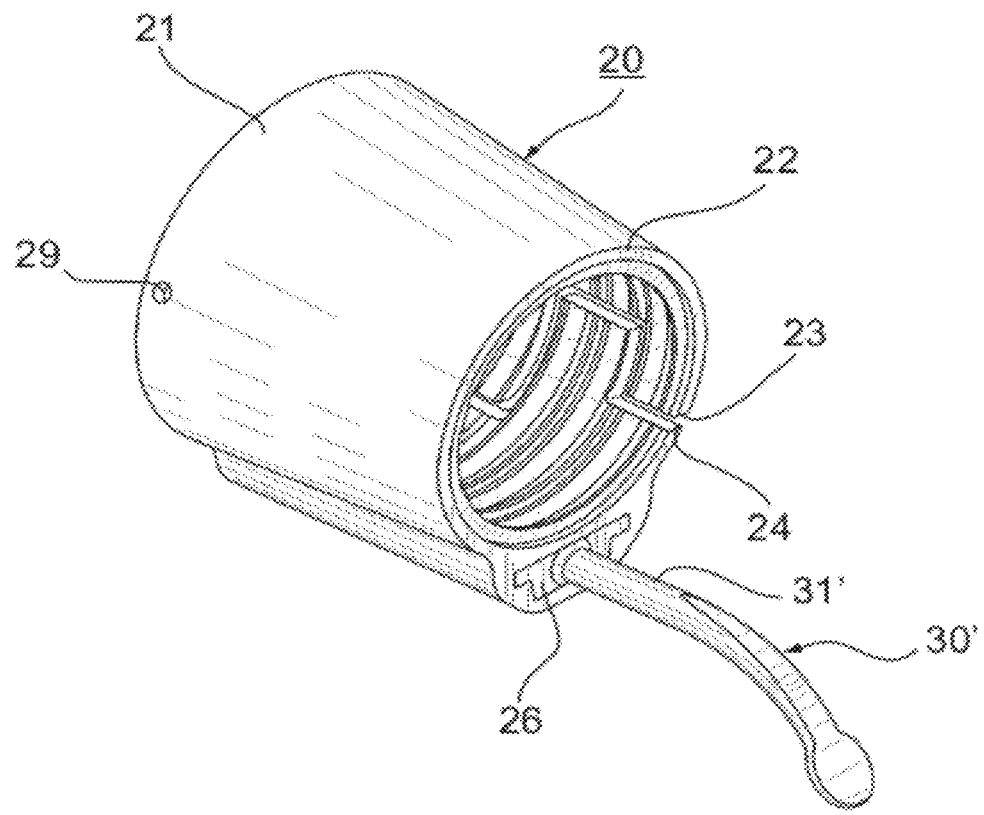
FIG. 6 illustrates a modification in the construction of the finger-mountable retractor of FIG. 3.

FIG. 6 illustrates the finger-mountable instrument described above except with a retractor 30' having a cylindrical shank 31' rather than a flat shank. Accordingly, a socket 26 would be suitably shaped to define a cylindrical passageway for receiving the cylindrical shank 31'. In this case, the retractor would be fixed within the socket by a friction fit.

Another modification illustrated in FIG. 6 is the provision of a small hole, shown at 29, through sleeve 20 near its proximal end 21. Hole 29 enables the attachment of a suture strand (not shown) which, when led through the port to the outside, facilitates tracing the instrument inside the body cavity during a HALS procedure. It will be appreciated that the finger-mountable sleeve illustrated in FIGS. 3-5, as well as those to be described below, could also be formed with such a hole for this purpose.

Figure 7:
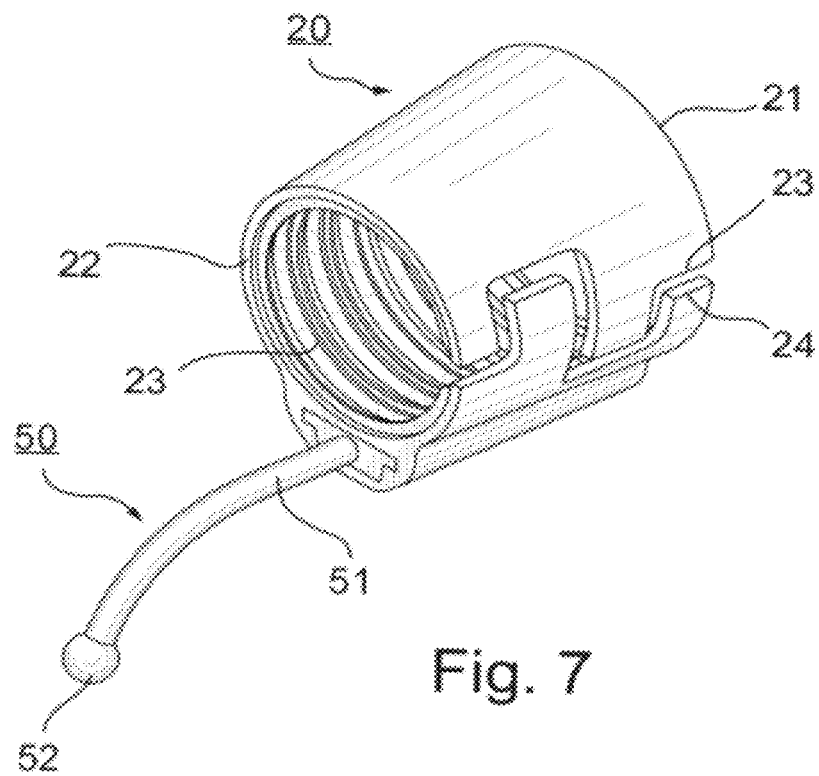
FIG. 7 illustrates a finger-mountable probe constructed in accordance with the present invention.

FIG. 7 illustrates the finger-mountable sleeve 20 for mounting another type of surgical instrument, in this case a probe 50 having a cylindrical shank 51 and a ball 52 at its outer end.

Figure 8:
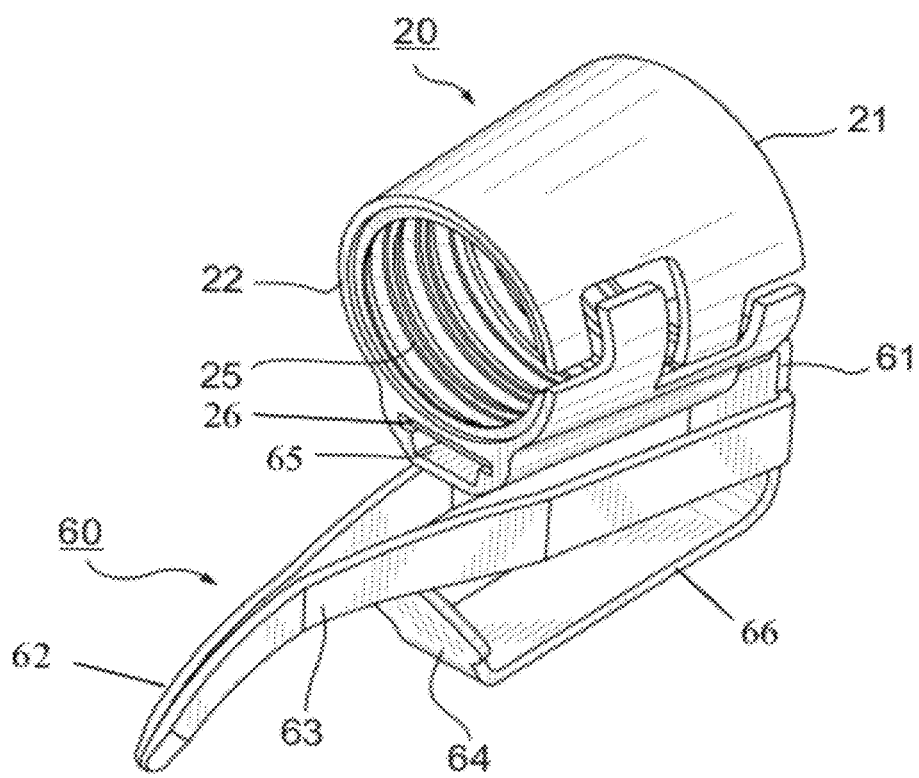
FIG. 8 illustrates a finger-mountable forceps or tweezers constructed in accordance with the present invention, also capable of mounting another surgical instrument, such as a retractor or probe, if desired.
Figure 9:
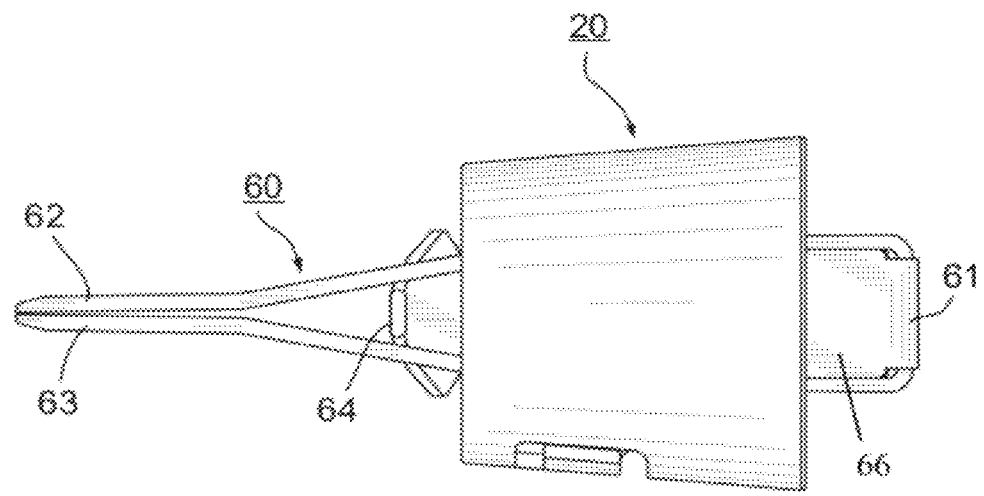
FIGS. 9 and 10 are top and bottom views, respectively, of the finger-mountable forceps or tweezers of FIG. 8.
Figure 10:
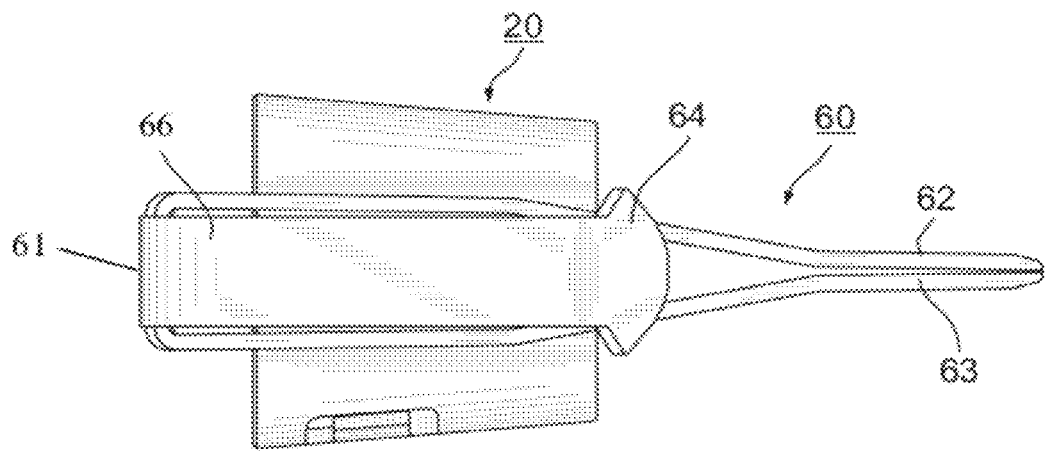

FIGS. 8-10 illustrate another construction of the finger-mountable sleeve 20 to include a surgical instrument assembly, generally designated 60, mounted in socket 26. Thus, surgical instrument assembly 60 further includes an elastic member 61 integrally formed at a mid-portion thereof with a pair of arms 62, 63 elastically-urged to a closed position to serve as a pair of forceps for grasping objects. Elastic member 61 is further integrally formed at one end with a mounting strip 65 folded to overlie the pair of arms 62, 63 for mounting the elastic member within socket 26, and at the opposite end with a finger-engageable strip 66 folded to underlie the pair of arms. Finger-engageable strip 66 terminates in a cam element 64 which is thereby movable by the elasticity of the elastic member between the pair of arms 62, 63 to cam them apart to an open position to release a grasped object. The two arms 62, 63 are thus normally biased to their closed position, as illustrated in FIG. 8, but are displaceable by cam element 64, when the distal end of its connecting strip 61 is manually pressed inwardly, to cam-apart the two arms 62, 63 to their open positions.

Thus, the construction illustrated in FIGS. 8-10 not only permit a probe, retractor, or other surgical instrument to be conveniently carried by the finger-mountable sleeve 20, but also permits the finger-mountable sleeve to be used as a forceps for grasping or releasing the various objects, such as tissue, sutures, suture needles, etc.

Figure 11:
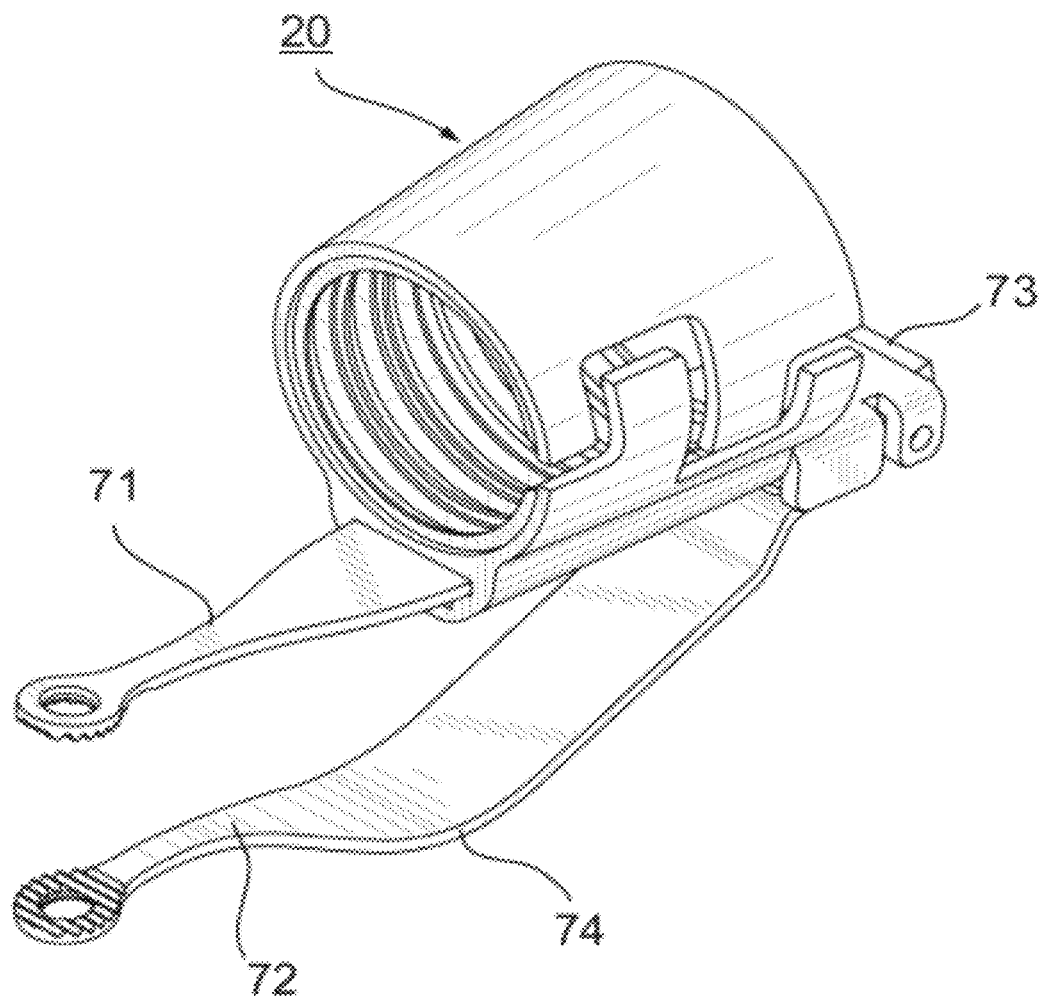
FIG. 11 illustrates yet another finger-mountable instrument, also in the form of a forceps or tweezers, constructed in accordance with the present invention.

FIG. 11 illustrates a further finger-mountable surgical instrument of basically the same construction as described above with respect to FIG. 3, and therefore corresponding elements have been identified by the same reference numerals. In the construction illustrated in FIG. 11, however, the socket 26 in the finger-mountable sleeve 20 is used for receiving one arm 71 of another type of forceps, generally designated 70, and the other arm 72 is integrally formed with an elastic strip 73 joined to arm 71. The two arms 71, 72 of forceps 70 are normally biased to their open positions, as illustrated in FIG. 11, but the lower arm 72 includes a bend 74 which is engageable by the finger of the user, to move arm 72 to a closed position with respect to arm 71.

All the components of the finger-mountable instruments described above can be made of a suitable biocompatible material according to conventional techniques, such as machining, forming, molding, riveting, etc.

While the invention has been described with respect to several preferred embodiments, it will be appreciated that these are set forth merely for purposes of example, and that many other variations, modifications and applications of the invention may be made.

What is claimed is:

1. A surgical instrument assembly, comprising:
    a sleeve dimensioned to be received on the outer end of a finger of a user
    and having an open proximal end for application to the outer end of the user's finger, an open distal end for exposing the outer tip of the user's finger when mounted thereon, and an inner diameter which decreases from said proximal end to said distal end for facilitating the application of the sleeve to the user's finger;
    said sleeve being of an elastic material, having a longitudinal split along its length to permit its diameter to be increased in order to accommodate fingers of different thicknesses, and
    integrally formed at one side with a socket for receiving a surgical instrument;
    and an elastic member integrally formed at a mid-portion thereof with a pair of arms elastically-urged to a closed position to serve as a pair of forceps for grasping objects; said elastic member being further integrally formed at one end with a mounting strip folded to overlie said pair of arms for mounting the elastic member within said socket, and at the opposite with a finger-engageable strip folded to underlie said pair of arms; said finger-engageable strip terminating in a cam element movable by the elasticity of the elastic member between said pair of arms to cam them apart to an open position to release a grasped object.

2. The surgical instrument assembly according to claim 1, wherein said longitudinal split is defined by two opposed edges having interengaging ribs and recesses of a length in the circumferential direction to accommodate a wide range of fingers thicknesses without pinching.

3. The finger mounting surgical instrument assembly according to claim 1, wherein the inner surface of said sleeve is formed with circumferentially-extending ribs to firmly grip the user's finger when the sleeve is applied thereto.

4. The surgical instrument assembly according to claim 1, wherein said sleeve is further formed with a hole therethrough for the attachment of a suture strand.

* * * * *